US012636474B2

(12) United States Patent
Britten et al.

(10) Patent No.: US 12,636,474 B2
(45) Date of Patent: May 26, 2026

(54) MICRONEEDLE ARRAY, MOLDING FOR MANUFACTURING A MICRONEEDLE ARRAY, AND METHOD FOR MANUFACTURING A MICRONEEDLE ARRAY

(71) Applicant: LTS Lohmann Therapie-Systeme AG, Andernach (DE)

(72) Inventors: Miriam Britten, Andernach (DE); Natasha Gannon, Koblenz (DE); Jörg Bender, Cologne (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 888 days.

(21) Appl. No.: 17/800,736

(22) PCT Filed: Jan. 22, 2021

(86) PCT No.: PCT/EP2021/051430

§ 371 (c)(1),
(2) Date: Aug. 18, 2022

(87) PCT Pub. No.: WO2021/164979

PCT Pub. Date: Aug. 26, 2021

(65) Prior Publication Data

US 2023/0098653 A1  Mar. 30, 2023

(30) Foreign Application Priority Data

Feb. 19, 2020  (DE) ..................... 10 2020 104 320.1

(51) Int. Cl.
*A61M 37/00* (2006.01)
*B29C 33/42* (2006.01)
*B29L 31/00* (2006.01)

(52) U.S. Cl.
CPC ......... *A61M 37/0015* (2013.01); *B29C 33/42* (2013.01); *A61M 2037/0053* (2013.01); *B29L 2031/7544* (2013.01)

(58) Field of Classification Search
CPC ...... A61M 37/0015; A61M 2037/0053; B29C 33/42; B29L 2031/7544
USPC ......................................................... 604/22
See application file for complete search history.

(56) References Cited

U.S. PATENT DOCUMENTS

| | | | |
|---|---|---|---|
| 6,866,808 B2 | 3/2005 | Widemann et al. | |
| 10,105,526 B2 | 10/2018 | Scherr et al. | |
| 11,452,854 B2 | 9/2022 | Sakazaki et al. | |
| 2008/0125743 A1 | 5/2008 | Yuzhakov | |
| 2009/0171314 A1 | 7/2009 | Ferguson | |
| 2017/0333342 A1 | 11/2017 | Wakamatsu | |
| 2020/0016388 A1* | 1/2020 | Jung ..................... | A61K 47/36 |

FOREIGN PATENT DOCUMENTS

| | | |
|---|---|---|
| CN | 108186006 A | 6/2018 |
| DE | 19936235 A1 | 2/2001 |
| EP | 2905047 A1 | 8/2015 |
| JP | 200789792 A | 4/2007 |

(Continued)

*Primary Examiner* — Phillip A Gray
(74) *Attorney, Agent, or Firm* — The Webb Law Firm

(57) ABSTRACT

A microneedle array has a plurality of microneedles, said microneedles being supported by a substrate. In order to improve the properties of the microneedle array, the substrate is in the form of a grid structure or comprises a grid structure.

17 Claims, 3 Drawing Sheets

(56) References Cited

FOREIGN PATENT DOCUMENTS

| JP | 2008302254 A | 12/2008 |
| JP | 2010063666 A | 3/2010 |
| JP | 2016069357 A | 5/2016 |
| JP | 2019198479 A | 11/2019 |

* cited by examiner

MICRONEEDLE ARRAY, MOLDING FOR MANUFACTURING A MICRONEEDLE ARRAY, AND METHOD FOR MANUFACTURING A MICRONEEDLE ARRAY

CROSS-REFERENCE TO RELATED APPLICATIONS

This application is the United States national phase of International Application No. PCT/EP2021/051430 filed Jan. 22, 2021, and claims priority to German Patent Application No. 10 2020 104 320.1 filed Feb. 19, 2020, the disclosures of which are hereby incorporated by reference in their entirety.

BACKGROUND OF THE INVENTION

Field of the Invention

The invention relates to a microneedle array, a molding for manufacturing a microneedle array, and a method for manufacturing a microneedle array.

Description of Related Art

Microneedles are used to deliver active ingredients directly into the skin, also known as transdermal delivery. For this purpose, the microneedles are just long enough to penetrate only the outer skin layers, but preferably not to reach nerves and blood vessels, thus leaving them unharmed. Nevertheless, microneedles create small holes in the upper skin layers, which significantly increases the absorption of active ingredients compared to a purely external application of active ingredients to the skin.

Microneedle arrays, which have a plurality of microneedles, for example attached to a carrier surface, can be used for short-term delivery or for long-term application. A preferred way of delivering the active ingredient from the microneedles into the skin is that areas of the microneedles containing active ingredient or the entire microneedle dissolve or detach and can thus be absorbed by the body through the skin. For this purpose, the microneedles are in particular, at least partially, made of water-soluble substances or materials, respectively. In addition to the direct delivery of active ingredients through the microneedles themselves, it is also possible for the microneedles to have pores or cavities or to be formed as hollow needles in order to enable active ingredient delivery to the skin in this way. Furthermore, microneedles can also be free of active ingredients. In this case, for example, the active ingredient can be applied externally to the outside of the microneedles, or a substance containing the active ingredient can be applied to the corresponding skin area only after the microneedles have been removed from the skin, in order to deliver active ingredients in this way using microneedles.

Microneedles can be made of ceramic, metal, or polymer, among other materials. Preferably, one or more active ingredient components are added to these materials, thus resulting in a formulation of the microneedles.

A common method of manufacturing microneedles involves casting the microneedles or entire microneedle arrays, respectively, for example using casting molds such as dies made of silicone. In particular due to the hydrophobic properties between the casting mold and the formulation applied to it, which is usually liquid, numerous problems arise in such manufacturing methods.

In such casting of the microneedle array, a liquid material, usually containing the active ingredient, is metered onto the molding, such as a die, so that the liquid enters the pyramidal depressions. If necessary, the same or a different material is metered further onto the die so that a bottom plate or support layer, respectively, is formed above the depressions. The support layer, which can be made of a different material, is thus connected with the microneedles arranged in the depressions. In particular, the support layer is required to demold the microneedles from the molding. The support layer is also required to ensure uniform power transmission of the application of the microneedles into the skin. Since not only the material forming the microneedle but also the material forming the support layer must dry, it is desirable for manufacturing reasons to keep the thickness of the support layer as low as possible. Furthermore, on the one hand, it is desirable for this layer to be as stiff as possible in order to enable good power transmission, in particular when applied into the skin. On the other hand, a high strength of the support layer prevents the microneedle array from adapting, for example, to unevenness of the skin or when applying the microneedle array to uneven areas of the skin.

SUMMARY OF THE INVENTION

An object of the present disclosure is to provide a microneedle array that ensures good application with sufficient stability. Furthermore, an independent object is to provide a suitable molding for manufacturing a microneedle array and a method for manufacturing a microneedle array.

The different objects are achieved by a microneedle array, a molding, and a manufacturing method.

The microneedle array according to the present disclosure has a plurality of microneedles. Here, the microneedles are particularly in the form of a pyramid and have a rectangular cross-section. The microneedles are connected with a support layer supporting the microneedles. In order to improve the support layer according to the present disclosure, the support layer is in the form of a grid structure or comprises a grid structure. Such a grid structure can provide sufficient stiffness for power transmission. On the other hand, there is a desired flexibility, for example, to be able to apply the microneedle array also to uneven areas of the skin or in curved areas.

It is particularly preferred that the grid structure is configured such that it connects at least a part of the microneedles with each other. Preferably, all microneedles are connected with each other via the grid structure. Here, it is basically possible that exclusively a grid structure is provided as a support layer and/or the grid structure is embedded in a support layer. Furthermore, these two configuration options can also be combined so that, for example, in partial areas of the microneedle array a grid structure is embedded in the support layer and in other areas exclusively a grid structure is provided.

Furthermore, it is preferred that the grid structure has crossing points which are at least partially connected with the microneedles. It is particularly preferred that all microneedles are connected with crossing points. If necessary, additional crossing points of grid structures can also be provided adjacent to the microneedles for further stiffening.

The grid structure can have grid bars with different angles to each other, wherein it is preferred that the grid structure is uniform and thus all bars run in a straight line and angles are provided at the crossing points. An angle of 90° at the crossing points is particularly preferred. However, it is also possible to at least partially provide grid bars that do not run in a straight line.

For connecting the microneedles with the bars of the grid structure, it is preferred that the material forming the microneedles is connected with the bars of the grid structure such that the material surrounds them in the area of the microneedles. If necessary, different materials may also be provided so that the microneedle is made of a first material, at least in the area of the tip, which in particular comprises the active ingredient. A further material, which in particular does not comprise the active ingredient and is therefore less expensive, can be used to create a connection between the microneedle and the bars of the grid structure. In particular, a connection between the microneedles is realized by the material of the microneedle or a further material such that the corresponding material surrounds the respective crossing points.

In another preferred embodiment, the grid structure is at least partially prefabricated. Here, the grid structure can have fibers, in particular textile fibers, and is particularly preferably made of such fibers.

Furthermore, it is possible to produce the grid structure by a linear application of a material. Particularly suitable materials are PVP, dextran, PLGA or the like. A production can be realized by linearly metering the material onto the upper side of the molding, such as the die in particular. It is also possible to combine the linear application for producing the grid structure with a prefabricated grid structure so that a prefabricated grid structure is at least partially linearly overmolded.

Furthermore, the inventions relates to a molding for manufacturing a microneedle array, in particular for manufacturing a microneedle array as described above.

The molding, which is a die in particular, has a plurality of depressions or cavities, respectively, in a base body. In particular, the depressions are depressions formed in the form of a pyramid for forming pyramidal microneedles. The depressions extend from an upper side of the base body. In a preferred embodiment, channels are provided in the upper side of the base body in order to form a grid structure. The channels can also be formed by providing protrusions or lugs. The grid structure is configured such that material containing in particular the active ingredient is first metered into the depressions and then the same or a different material is metered such that the channels located on the upper side of the base body are also filled with material.

Preferably, at least a part of the depressions is connected with channels. In particular, the crossing points of channels are at least partially arranged such that the channels cross in the area of the depressions. In this respect, in a preferred further embodiment of the present disclosure, each depression is connected with at least one, in particular at least two channels. At least a part of the channels is arranged or configured such that it connects neighboring depressions with each other.

In particular in a preferred further embodiment, the above-described molding can be used to manufacture a microneedle array according to the invention a described above. It is also possible to insert a grid structure into the channels. For example, fibers of a grid structure could be inserted into part of the channels. Said fibers are then surrounded or overmolded, respectively, by a material in order to form a complete grid structure.

Furthermore, the present disclosure relates to a method of a microneedle array, wherein in particular manufacturing a microneedle array according to the present disclosure is preferred.

In a first method step, a material such as a liquid, which in particular contains the active ingredient, is metered into depressions of a molding. The first method step may also include several individual steps, in each of which in particular different materials are metered. Here, it is preferred to use a molding according to the present disclosure as described above. In the next step, the material is linearly applied to an upper side of the molding in order to form a grid structure. Here, as described above with reference to the molding according to the present disclosure, the molding can have channels or also a substantially even surface to which a respective grid structure is applied. In this case, it is preferred that a material other than the material used to form the microneedle tip is applied.

It is also preferred that the linear application is at least partially realized such that at least a part of the lines cross depressions or are connected with the rear side of the microneedles formed in the depressions, respectively. Furthermore, it is preferred that the linear application is realized such that at least a part of the crossing points of the lines is arranged in the area in particular above the depressions.

The microneedle array according to the present disclosure, which is preferably manufactured in the above-described molding and/or by the above-described method, has a number of advantages as compared to known microneedle arrays. Due to the grid structure, it is in particular possible to arrange the microneedle array also on uneven or curved areas of the skin and to still realize a uniform penetration of the microneedles into the skin so that a good delivery of active ingredients is guaranteed. Moreover, the flexibility of the microneedle array is improved by providing a grid structure. When designing a microneedle array according to the present disclosure with spaces between the bars of the grid structure, this moreover has the advantage that moisture can easily reach the skin and in this respect that dissolution of the microneedles or a part of the microneedles is improved. This is in particular advantageous if the grid structure or the support layer, respectively, is made of a non-dissolving material. It is also advantageous, particularly in the case of longer application of the microneedle array, to fix the microneedle array to the skin with a plaster, wherein the plaster can then also be bonded to the skin in the spaces of the grid structure, and a more secure fixation of the microneedle array to the skin is ensured.

Another advantage of a grid structure is that it has less mass to be dissolved.

In the following, the present disclosure is described in more detail by means of preferred embodiments with reference to the accompanying drawings.

DETAILED DESCRIPTION

Figures 1, 2, 3:
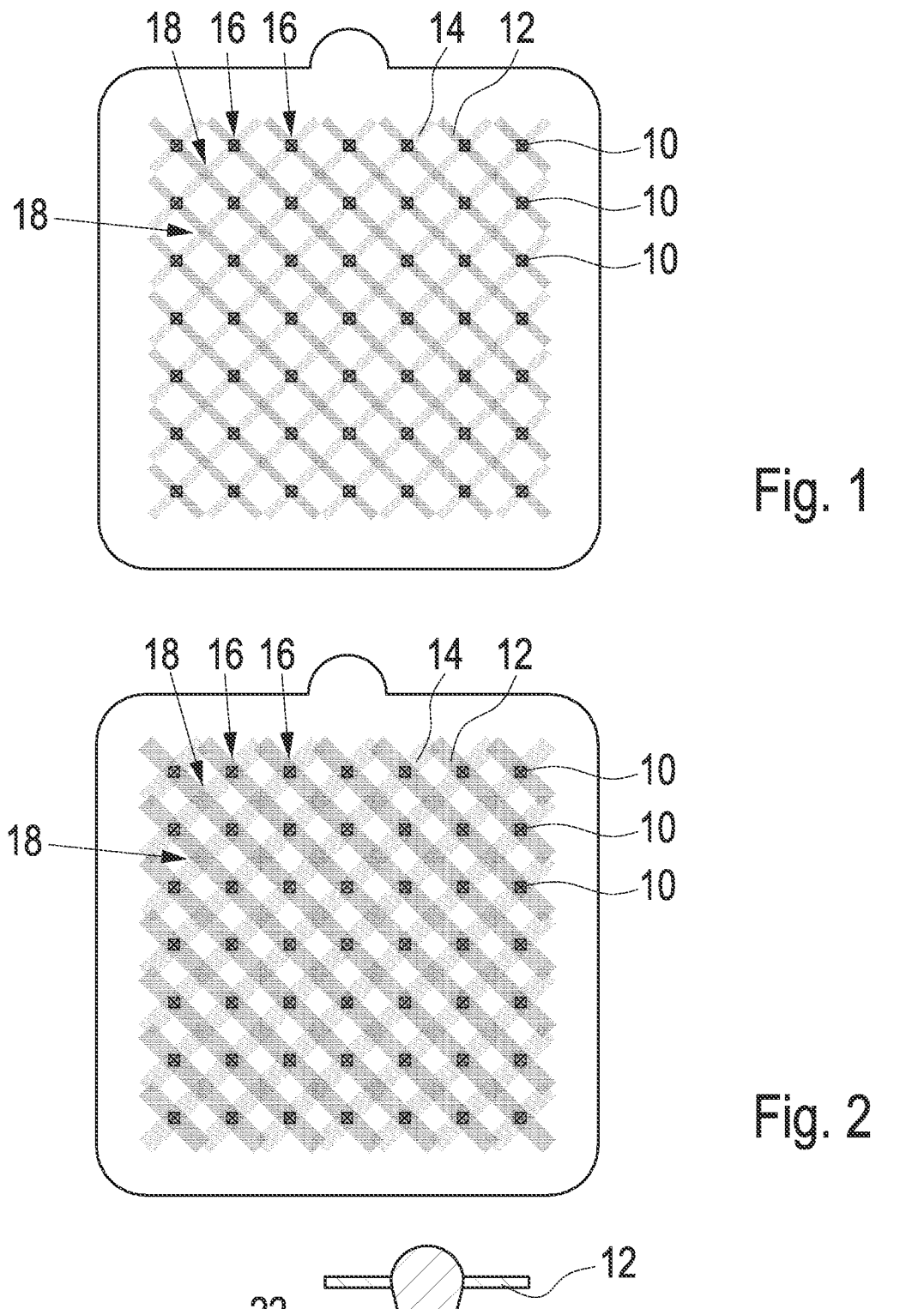
FIG. 1 shows a schematic plan view of a microneedle array according to a first preferred embodiment.
FIG. 2 shows a schematic plan view of a microneedle array according to a second preferred embodiment.
FIG. 3 shows a schematic sectional view of a microneedle in longitudinal direction.

In the drawings, different embodiments of microneedle arrays are shown schematically. For convenience, the microneedles 10 are illustrated as squares.

In the exemplary embodiment shown in FIG. 1, a grid structure with bars 12, 14 is formed. The bars 12, 14 forming the grid structure are arranged perpendicular to each other. Here, the bars are arranged such that a part of the crossing points 16 is arranged above the microneedles 10. Further crossing points 18 are respectively arranged between the microneedles 10.

As can be seen in FIG. 2, the bars can of course also have a width that is slightly larger than the base area of the microneedles 10.

The microneedles 10 are preferably pyramidal and in particular have a rectangular, preferably square cross-section. The depressions of the die are correspondingly formed.

In the sectional view shown in FIG. 3, a microneedle 10 is shown. The microneedle is made in a lower area 20 forming the tip of the needle by a material comprising in particular the active ingredient. In particular, the needle tip can also be formed with multiple layers, wherein in particular different materials are metered successively. Moreover, a bar 12 of a grid structure is shown. A further material 22 is provided for connecting the needle tip 20 with the bar 12 of the grid structure. Said material encloses the bar 12 in the area of the upper side of the needle 10 in a drop shape.

Figure 4:
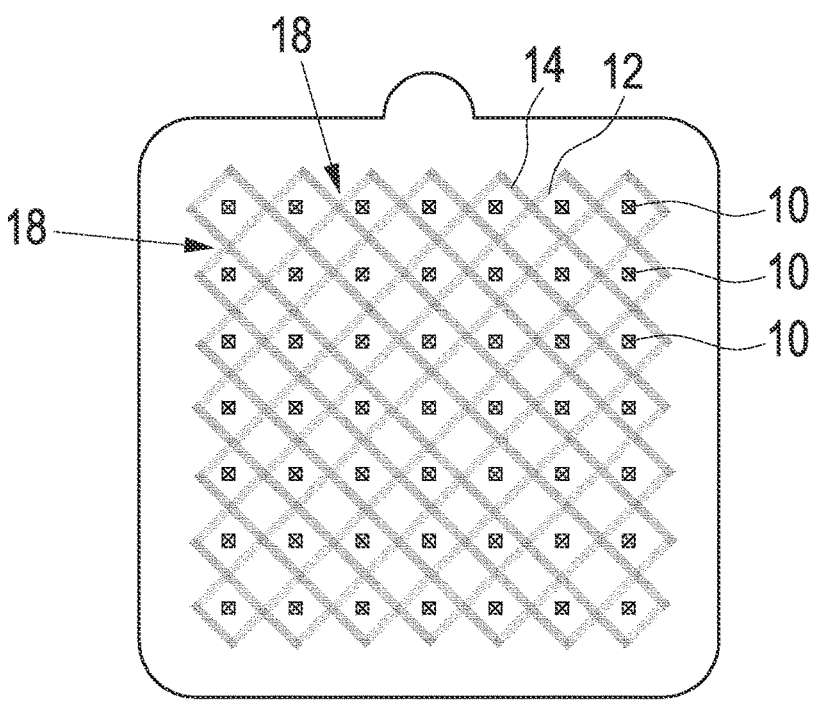
FIG. 4 shows a schematic plan view of a microneedle array according to a third preferred embodiment.
Figure 5:
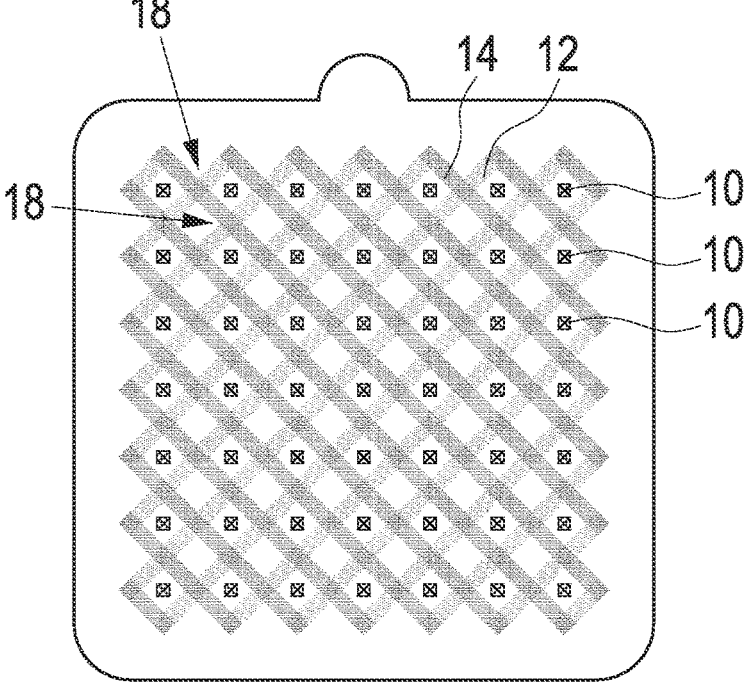
FIG. 5 shows a schematic plan view of a microneedle array according to a fourth preferred embodiment.

Similar grid structures are shown in FIGS. 4 and 5, wherein said grid structures are arranged such that the microneedles are located in the spaces of the grid structure. In this respect, these are grid structures that are embedded or inserted in a support layer, respectively. Furthermore, said grid structures can also be made of a different material.

When filling individual cavities to form the microneedles, it is also possible to provide in particular the further material 22 in such a quantity that the material of adjacent areas flows together or joins together, respectively. Thus, a gird structure is formed.

Alternatively, a material can be linearly applied to the upper side 26 of the base body or the die 28, respectively, in order to form a grid structure, wherein this is preferably realized such that the lines cross above the cavities or depressions 24, respectively.

Figures 6, 7:
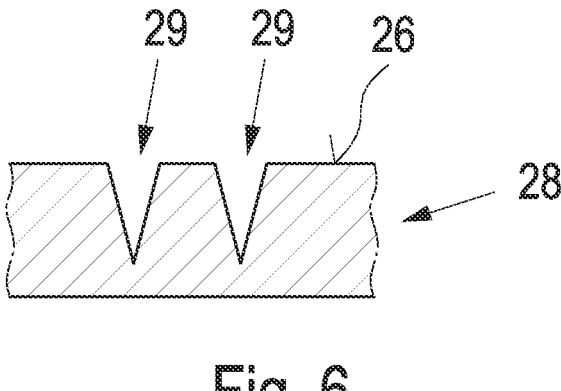
FIG. 6 and FIG. 7 show schematic sectional views of dies for manufacturing microneedle arrays according to the invention.

FIG. 6 and FIG. 7 show schematically simplified illustrations of possible configurations of dies.

In the simple configuration shown in FIG. 6, pyramidal depressions 24 are provided which, from an even surface 26 of the die, extend inwards or, in FIG. 6, downwards, respectively. The microneedles 10 are produced by filling the cavities 24. In particular, by filling with a further material 22 (compare FIG. 3), a grid structure can be produced by bonding material of neighboring cavities together on the upper side 26 of the die 28.

Additionally or alternatively, a prefabricated grid structure may be arranged on the upper side 26.

In another embodiment of a die 30 (FIG. 7), in addition to the cavities 24 provided in the die 30 for forming the microneedles 10, depressions 34 are formed in an upper side 32 of the die. Said depressions 34 are formed to be linear or channel-shaped and connect neighboring cavities 24 with each other. By filling the depressions 34, in particular with a further material 22, a grid structure can be produced in a simple manner. If necessary, a prefabricated grid structure can be inserted into the channel-shaped depressions 34 for stiffening while improving the structure and quality, the grid structure being then at least partially enclosed by the further material 22.

The invention claimed is:

1. A microneedle array comprising:
   a plurality of microneedles; and
   a support layer supporting the plurality of microneedles,
   wherein the support layer is formed as a grid structure or comprises a grid structure,
   wherein the grid structure has a plurality of crossing points, the crossing points being at least partially connected with the plurality of microneedles, and
   wherein a material forming the plurality of microneedles surrounds at least one crossing point of the grid structure.

2. The microneedle array according to claim 1, wherein the grid structure connects the plurality of microneedles with each other.

3. The microneedle array according to claim 1, wherein a plurality of bars of the grid structure are perpendicular to each other.

4. The microneedle array according to claim 1, wherein the grid structure is prefabricated.

5. The microneedle array according to claim 1, wherein the grid structure is produced by linearly applying a material that essentially comprises PVP.

6. The microneedle array according to claim 1, wherein the grid structure has a plurality of fibers which are essentially made from textiles.

7. The microneedle array according to claim 1, wherein the grid structure is produced by a material forming the plurality of microneedles.

8. A molding for manufacturing a microneedle array comprising:
   a base body having a plurality of depressions,
   wherein a plurality of channels are provided for forming a grid structure on an upper side of the base body, such that the molding yields a microneedle array comprising:
   a plurality of microneedles; and
   a support layer supporting the plurality of microneedles,
   wherein the support layer is formed as a grid structure or comprises a grid structure,
   wherein the grid structure has a plurality of crossing points, the crossing points being at least partially connected with the plurality of microneedles, and
   wherein a material forming the plurality of microneedles surrounds at least one crossing point of the grid structure.

9. The molding according to claim 8, wherein at least one of the plurality of depressions is connected with one of the plurality of channels.

10. The molding according to claim 8, wherein at least one of the plurality of depressions is connected with at least one of the plurality of channels.

11. The molding according to claim 8, wherein at least one of the plurality of channels connects its neighboring plurality of depressions with each other.

12. A method for manufacturing a microneedle array, the method comprising the steps of:
   metering one or several materials into depressions extending from an upper side of a molding; and
   linearly applying a material to the upper side of the molding in order to form a grid structure, such that the method for manufacturing a microneedle array yields a microneedle array comprising:

a plurality of microneedles; and a support layer supporting the plurality of microneedles, wherein the support layer is formed as a grid structure or comprises a grid structure, wherein the grid structure has a plurality of crossing points, the crossing points being at least partially connected with the plurality of microneedles, and wherein a material forming the plurality of microneedles surrounds at least one crossing point of the grid structure.

13. The method according to claim 12, wherein linearly applying the material is realized such that at least a part of one line crosses the depressions provided in the molding.

14. The method according to claim 12, wherein linearly applying the material is realized such that at least a part of one nodal point formed by the grid structure is arranged in the area of the depressions.

15. The microneedle array according to claim 1, wherein the plurality of microneedles are made of a first material, wherein the first material is located in at least an area of one or more of a tip of each of the plurality of microneedles, wherein the first material comprises an active ingredient, wherein the support layer is made of a second material, and wherein the second material does not comprise the active ingredient of the first material.

16. The microneedle array according to claim 1, wherein the grid structure comprises a plurality of bars with spaces between the bars.

17. The molding according to claim 8, wherein the plurality of channels comprise crossing points that are at least partially arranged so that the crossing points of the plurality of channels cross in an area of each of the plurality of depressions.

* * * * *